(12) United States Patent
Jigami et al.

(10) Patent No.: US 7,741,087 B2
(45) Date of Patent: Jun. 22, 2010

(54) LIPID REMODELING OF GPI-ANCHORED PROTEINS

(75) Inventors: Yoshifumi Jigami, Ibaraki (JP); Takehiko Yoko-O, Ibaraki (JP); Mariko Umemura, Ibaraki (JP); Morihisa Fujita, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 139 days.

(21) Appl. No.: 11/835,249

(22) Filed: Aug. 7, 2007

(65) Prior Publication Data
US 2008/0233608 A1 Sep. 25, 2008

(30) Foreign Application Priority Data
Aug. 11, 2006 (JP) .............................. 2006-220491

(51) Int. Cl.
C12N 9/00 (2006.01)
C12N 1/20 (2006.01)
C12N 15/00 (2006.01)
C07H 21/04 (2006.01)

(52) U.S. Cl. ................. 435/183; 435/252.3; 435/320.1; 536/23.2

(58) Field of Classification Search ....................... None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AAY66723, published Apr. 5, 2000.*
Accession S19457, published Mar. 31, 1992.*
A. Goffeau et al., "Vacuolar membrane protein that seems to be involved in Mn2+ homeostasis; mutant is dependent on activation of the unfolded protein response pathway for viability; Per1p [*Saccharomyces cerevisiae*]", Accession NP_009973 [GI:6319893] NCBI, Dec. 20, 2005 URL http://www.ncbi.nlm.nih.gov/sviewer/viewer.fcgi?6319892:NCB1:12403812.
R. L. Strusberg et al., "Homo sapiens perl-like domain containing 1, mRNA, (cDNA clone)", Accession: BC010652 [GI: 14714985] NCBI, Jun. 15, 2006 URL, http://www.ncbi.nlm.nih.qov/entrez/viewer.fcgi?db=nuccore&id=14714985.
Morihisa Fujita et al., "Inositol Deacylation by Bst1p Is Required for the Quality Control of Glycosylphosphatidylinositol-anchored Proteins" Molecular Biology of the Cell, vol. 17, Feb. 2006, pp. 834-850.
Regine Bossom et al., "GUP1 of *Saccharomyces cerevisiae* Encodes an O-Acyltransferase Involved in Remodeling of the GPI Anchor", Molecular Biology of the Cell, vol. 17, 2636-2645, Jun. 2006.
Maya Schuldiner et al., "Exploration of the Function and Organization of the Yeast Early Secretory Pathway through an Epistatic Miniarray Profile", Cell, vol. 123, pp. 2-70.

* cited by examiner

*Primary Examiner*—Christian L Fronda
(74) *Attorney, Agent, or Firm*—Stephen A. Bent; Foley & Lardner LLP

(57) ABSTRACT

This invention provides proteins and genes thereof involved in the GPI lipid remodeling process and, thereby and constructing a system for screening for useful substances such as anticancer agents and a system for detecting abnormalities in the GPI lipid remodeling process.

3 Claims, 10 Drawing Sheets

LIPID REMODELING OF GPI-ANCHORED PROTEINS

BACKGROUND OF THE INVENTION

1. Field of the Invention

The present invention relates to novel genes and proteins involved in carcinogenesis and the GPI biosynthesis process.

2. Background Art

It has been known that, in some breast cancer cells or gastric cancer cells, a chromosomal region referred to as 17q12 is amplified and that the expression level of a gene of unknown function that is referred to as PERLD1 in the region increases (Non-Patent Document 1: Nezu, M., Nishigaki, M., Ishizuka, T., Kuwahara, Y, Tanabe, C., Aoyagi, K., Sakamoto, H., Saito, Y, Yoshida, T., Sasaki, H., and Terada, M. Jpn. J. Cancer Res. 93: 1183-1186 (2002); and Non-Patent Document 2: Katoh, M. and Katoh, M. Int. J. Oncol. 22: 1369-1374 (2003)).

The glycosylphosphatidylinositol (GPI) anchor is a form of posttranslational modification of proteins. GPI anchors enable extracellularly secreted proteins to stay in the vicinity of the cell surface. Intensive studies have been conducted on the biosynthesis mechanism of GPI-anchored proteins. However, on the lipid remodeling steps following the addition of a GPI to a protein, only some aspects have started to become clear (Non-Patent Document 3: Bosson, R., Jaquenoud, M., and Conzelmann, A. Mol. Biol. Cell 17: 2636-2645 (2006)).

Recent studies revealed that genes in the GPI biosynthesis system may be involved in carcinogenesis. However, all of the genes that have been found in the GPI synthesis system and reported as oncogenes encode transamidases, which transfer GPI to a protein (Non-Patent Document 4: Guo, Z., Linn, J. F., Wu, G. Anzick, S. L., Eisenberger, C. F., Halachmi, S., Cohen, Y, Fomenkov, A., Hoque, M. O., Okami, K., Steiner, G, Engles, J. M., Osada, M., Moon, C., Ratovitski, E., Trent, J. M., Meltzer, P. S., Westra, W. H., Kiemeney, L. A., Schoenberg, M. P., Sidransky, D., and Trink, B. Nat. Med. 10, 374-381 (2004); and Non-Patent document 5: Ho, J. C., Cheung, S. T., Patil, M., Chen, X. and Fan, S. T. Int. J. Cancer 119, 1330-1337 (2006)).

SUMMARY OF THE INVENTION

As described above, no information has been provided on whether genes or proteins (excluding transamidase) used in the GPI synthesis system such as those involved in lipid remodeling are associated with carcinogenesis.

In addition, it has been unclear which types of genes or proteins are involved in the step where phosphatidylinositol (PI) is converted into lysophosphatidylinositol (lyso-PI) in GPI lipid remodeling. Further, in such situation, it is natural that methods for measuring the activity of such protein or simple methods for detecting abnormalities in GPI lipid remodeling have not been established.

It is an objective of the present invention to reveal the enzyme proteins and the genes thereof involved in the lipid remodeling process or to elucidate the mechanism of such process so as to construct a system for screening for useful substances such as novel anticancer agents and the like based on the elucidated mechanism. It is another objective of the present invention to construct a system for detecting abnormalities in GPI lipid remodeling so as to elucidate the relationship between the lipid remodeling process and carcinogenesis. That is, the present invention is intended to contribute to the development of research on novel cancer therapies or diagnostics.

As a result of intensive studies directed to the above objectives, the present inventors have found that the yeast PER1 gene and a protein encoded by the gene are involved in the GPI lipid remodeling process. Further, we have found that genes and proteins homologous to the PER1 gene and protein derived from non-yeast organisms, such as the human PERLD1 gene and protein, are also involved in GPI lipid remodeling. Based on these findings, we succeeded in developing a system for screening for useful substances such as novel anticancer agents and a system for detecting abnormalities in the GPI lipid remodeling process. This has led to the completion of the present invention. Specifically, the present invention is described as follows.

(1) An enzyme protein comprising the amino acid sequence represented by SEQ ID NO: 2, or comprising an amino acid sequence derived from the amino acid sequence by deletion, substitution, or addition of one or more amino acids and having an activity of converting the phosphatidylinositol structure of a GPI-anchored protein to a lysophosphatidylinositol structure.

(2) An enzyme protein having a 39% or more homology to the protein according to (1).

(3) An enzyme protein comprising the amino acid sequence represented by SEQ ID NO: 4, or comprising an amino acid sequence derived from the amino acid sequence by deletion, substitution, or addition of one or more amino acids and having an activity of converting the phosphatidylinositol structure of a GPI-anchored protein to a lysophosphatidylinositol structure.

(4) An enzyme reagent comprising the protein according to any one of (1) to (3), which is for use in converting the phosphatidylinositol structure of a GPI-anchored protein to a lysophosphatidylinositol structure.

(5) A reagent for screening for a substance which promotes or inhibits the activity of the enzyme protein according to any one of (1) to (3) of converting the phosphatidylinositol structure of a GPI-anchored protein to a lysophosphatidylinositol structure, wherein the reagent at least comprises said enzyme protein.

(6) The reagent according to (5), wherein the substance that inhibits the activity of the enzyme protein is a candidate substance for an anticancer agent.

(7) A gene encoding the protein according to any one of (1) to (3).

(8) A gene comprising the nucleotide sequence represented by SEQ ID NO: 1, or comprising a nucleotide sequence derived from the nucleotide sequence by deletion, substitution, or addition of one or more nucleotides and encoding an enzyme protein having an activity of converting the phosphatidylinositol structure of a GPI-anchored protein to a lysophosphatidylinositol structure.

(9) A gene comprising the nucleotide sequence represented by SEQ ID NO: 3, or comprising a nucleotide sequence derived from the nucleotide sequence by deletion, substitution, or addition of one or more nucleotides and encoding an enzyme protein having an activity of converting the phosphatidylinositol structure of a GPI-anchored protein to a lysophosphatidylinositol structure.

(10) A recombinant vector comprising the gene according to any one of (7) to (9).

(11) A transformant into which the recombinant vector according to (10) has been introduced.

(12) A yeast transformant which is deficient in the PER1 gene and is introduced with a recombinant vector comprising a PERLD1 gene.

(13) A host for use in preparation of the yeast transformant according to (12), wherein it is a PER1 gene-deficient yeast.

(14) A test material for use in screening for a substance that promotes or inhibits the lipid remodeling process for a GPI-anchored protein, comprising at least the yeast transformant according to (12), a PER1-deficient yeast, a yeast in which the PER1 gene is overexpressed, or a wild-type yeast.

(15) The test material according to (14), wherein the substance that promotes or inhibits the lipid remodeling process for a GPI-anchored protein is a candidate substance for an anticancer agent.

(16) A method for screening for a substance that promotes or inhibits the lipid remodeling process for a GPI-anchored protein, comprising the steps of:

culturing the yeast according to (14) in a medium containing a candidate substance that may promote or inhibit the lipid remodeling process for a GPI-anchored protein; and measuring amounts of GPI-anchored proteins existing in DRM fractions or amounts of GPI-anchored proteins released into the extracellular medium.

(17) An antibody that recognizes a PER1 or PERLD1 gene product.

(18) A method for detecting abnormalities in the lipid remodeling process for a GPI-anchored protein, comprising measuring amounts of GPI-anchored proteins released from cells into the extracellular medium.

(19) The method according to (18), wherein the extracellular medium is blood.

(20) A method for producing a GPI-anchored protein, comprising the steps of:

culturing cells with abnormalities in the lipid modeling process; and recovering a GPI-anchored protein released into the extracellular medium.

The present invention is innovative in that it identifies for the first time the enzyme proteins and the genes thereof involved in the GPI lipid remodeling process. In addition, according to the present invention, the relationship between abnormalities in the GPI lipid modeling process and extracellular release of GPI-anchored proteins is revealed. Thus, it has become possible to readily detect abnormalities in the GPI lipid remodeling process by measuring amounts of extracellular GPI anchors. Further, with the use of such detection means, it is possible to screen for anticancer agents which direct to a novel target, namely, lipid remodeling. The present invention also contributes to early detection of cancers and determination of the stages thereof. On the other hand, with the use of cells with abnormalities in lipid remodeling, glycoproteins to which GPIs have been attached can be extracellularly secreted such that it is possible to separate and recover such glycoproteins. Accordingly, it becomes possible to prepare GPI-anchored glycoproteins or sugar chains that have been attached to such proteins, leading to a contribution to the production of useful substances.

DESCRIPTION OF THE PREFERRED EMBODIMENTS

Figure 1:
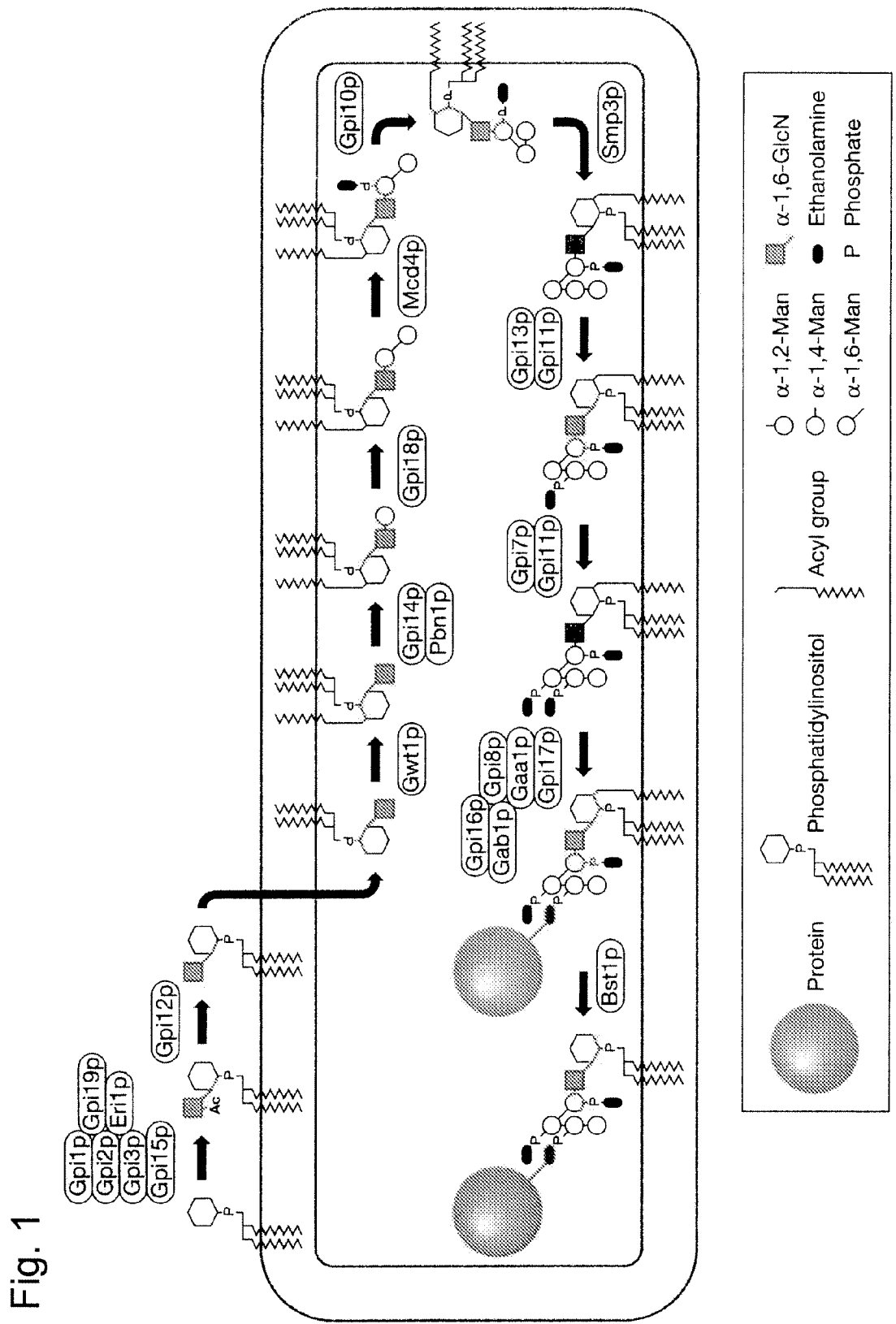
FIG. 1 shows a schematic diagram of the GPI biosynthetic pathway.
Figure 2:
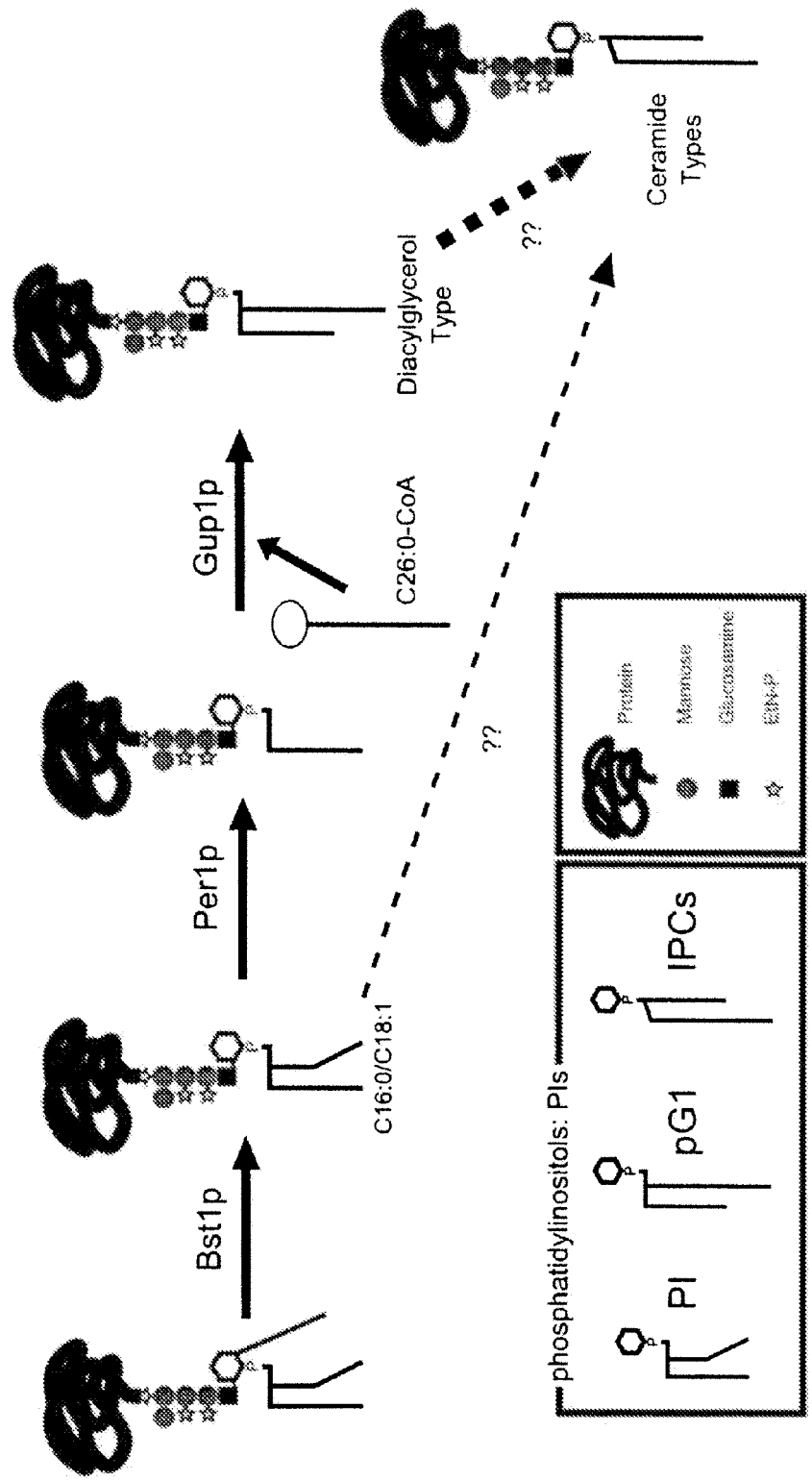
FIG. 2 shows the process of lipid remodeling that takes place after transfer of GPI to a protein.

The GPI biosynthetic pathway is a pathway in which sugars and ethanolamine phosphate are sequentially added to phospholipid phosphatidylinositol and the resulting complete precursor is then transferred to a protein (FIG. 1). The lipid remodeling process is a process following the addition of GPI to a protein. In this process, the phosphatidylinositol (PI) structure in a GPI-anchored protein is converted into the lysophosphatidylinositol (lyso-PI) structure, then into the diacylglycerol (pG1) type, and finally into the ceramide (IPC) type (FIG. 2).

Specifically, a fatty acid at the sn-2 position of the PI structure is an unsaturated fatty acid prior to lipid remodeling. A Per1 protein functions to remove such fatty acid at the sn-2 position. Thus, PI becomes a so-called "one-legged" lyso-PI in which fatty acid is attached only to the sn-1 position. Thereafter, a longer saturated fatty acyl chain is added to the sn-2 position by a Gup1 protein. Such structure comprising a long saturated fatty acyl chain is referred to as pG1 type.

Such lipid remodeling process of GPI-anchored proteins was revealed for the first time by combining the findings of the present inventors with the findings presented by Bosson, R. et al. (supra).

The PER1 gene of the present invention is a gene derived from budding yeast (*Saccharomyces cerevisiae*). An enzyme protein encoded by the gene (hereafter, referred to as Per1 protein in some cases) has a function of converting the phosphatidylinositol (PI) structure of GPI-anchored protein into a lysophosphatidylinositol (lyso-PI) structure during the above lipid remodeling process. The nucleotide sequence of the gene is represented by SEQ ID NO: 1. In addition, the amino acid sequence of the enzyme protein is represented by SEQ ID NO: 2.

The present invention encompasses not only the budding yeast PER1 gene and a protein encoded by the gene but also genes homologous to such gene and proteins homologous to such protein. Specifically, a gene or protein with 39% or more homology at the protein level to the above PER1 gene or protein may be included in a gene or protein having a function similar thereto. Examples of important genes and proteins homologous to the PER1 gene and the protein include the human PERLD1 gene and an enzyme protein encoded by the gene (hereafter, referred to as PERLD1 protein in some cases). The nucleotide sequence of the human PERLD1 gene is represented by SEQ ID NO: 3. The amino acid sequence of the PERLD1 protein is represented by SEQ ID NO: 4. In the Examples described below, it is confirmed that the human PERLD1 protein has a function similar to that of the Per1 protein.

These PER1 and PERLD1 genes can be obtained by PCR or the like with the use of a commercially available cDNA library or the like. The Per1 and PERLD1 proteins can be obtained by genetic engineering techniques with the use of such genes.

Homologies at the protein level to budding yeast Per1p are 40% in the case of human (PERLD1), 45% in the case of fission yeast, 44% in the case of *Drosophila melanogaster*, 42% in the case of *Xenopus laevis*, 41% in the case of rat, 46% in the case of rice, 45% in the case of mouse, 47% in the case of *Arabidopsis thaliana*, 40% in the case of nematode, and 39% in the case of zebrafish.

In addition, homologies at the protein level to PERLD1 are 49% in the case of fission yeast, 57% in the case of *Drosophila melanogaster*, 85% in the case of *Xenopus laevis*, 93% in the case of rat, 51% in the case of rice, 92% in the case of mouse, 51% in the case of *Arabidopsis thaliana*, 47% in the case of nematode, and 80% in the case of zebrafish. It can be said that the above examples have functions identical to the function of Per1 or PERLD1 and thus they constitute the Per1 family.

It is possible to confirm whether the genes (derived from the above examples such as fission yeast, *Drosophila melanogaster, Xenopus laevis*, rat, rice, mouse, *Arabidopsis thaliana*, nematode, and zebrafish) and proteins produced from such genes have functions identical to those of the PER1 gene and protein by ligating a gene homologous to PER1, which is derived from a non-yeast organism among the above examples, to a budding yeast expression vector, introducing the vector into a per1 disruptant, and examining Calcofluor White sensitivity and temperature sensitivity of the resulting transformant.

According to the present invention, the Per1 and PERLD1 proteins or proteins homologous thereto (derived from non-yeast organisms) include not only proteins comprising their native amino acid sequences but also proteins comprising amino acid sequences derived from such amino acid sequences by deletion, substitution, or addition of one or more amino acid residues as long as a protein has the function of converting the phosphatidylinositol structure of GPI-anchored protein into a lysophosphatidylinositol structure. In addition, according to the present invention, the PER1 and PERLD1 genes or genes homologous thereto (derived from non-yeast organisms) include not only genes comprising their native nucleotide sequences but also genes comprising nucleotide sequences derived from such nucleotide sequences by deletion, substitution, or addition of one or more nucleotides as long as such genes encodes a protein having the function of converting the phosphatidylinositol structure of a GPI-anchored protein into a lysophosphatidylinositol structure.

It is possible to obtain proteins (derived from non-yeast organisms) that are homologous to the above Per1 protein by carrying out Southern hybridization with the use of the PER1 gene or DNA encoding the PERLD1 gene as a probe and isolating hybridized DNA, followed by in vitro or in vivo translation.

Specifically, a wheat germ or *Escherichia coli* lysate system may be used as an in vitro translation system. For an in vivo translation system, a method whereby the above DNA is ligated to an *Escherichia coli* expression vector so as to cause the expression in *Escherichia coli*, a method whereby the above DNA is ligated to a yeast expression vector so as to cause the expression in yeast cells, or the like can be used.

It is possible to obtain the Per1 and PERLD1 proteins, for example, by inserting the genes thereof into yeast expression vectors so as to produce such proteins in yeast cells. Specifically, the PER1 or PERLD1 gene is inserted between a TDH3 promoter and a TDH3 terminator of a budding yeast expression vector YEp352GAP. Then, the resulting plasmid is introduced into a yeast cell by the lithium acetate method or the like, and such yeast cell is allowed to proliferate in a nutrient medium. Accordingly, the cultured yeast cells produce large amounts of PER1 or PERLD1 gene products. In addition, upon plasmid construction, a tag gene such as hemagglutinin (HA) or green-fluorescent protein (GFP) can be added to the PER1 or PERLD1 gene.

As described in the Background Art, increased expression levels of the PERLD1 gene are observed in cancer cells. Further, as described above, the function of PERLD1 is identical to the function of PER1. In view of these facts, it is suggested that carcinogenesis is induced when the process of converting PI into lyso-PI is promoted during GPI lipid remodeling. Thus, it is understood that a substance that inhibits the activity of converting PI of GPI-anchored protein into lyso-PI can be a candidate for an anticancer agent.

The Per1 protein, the PERLD1 protein, or a protein homologous thereto (derived from non-yeast organisms) can be used as a reagent for screening for the above inhibitor or activator. For instance, changes in the activity of converting into a lyso-PI form may be measured by adding, for example, a candidate substance for a useful substance, such as an anticancer agent, to an enzyme activity measurement system for screening, such system comprising the above proteins and the PI form of a GPI-anchored protein (e.g., Gas1p) that serves as a substrate. A substance that inhibits such activity can be a candidate substance for an anticancer agent. In addition, proteins used are not necessarily purified. Microsomal membrane fractions comprising such proteins may be used.

For instance, when Flag-Gas1p is allowed to react with microsomal membrane fractions that have been prepared from a wild-type strain, a band corresponding to the lyso-PI form shifts to the earlier fraction. It is possible to find a substance that inhibits the activity of converting PI into lyso-PI by adding a candidate substance for an anticancer agent to such activity measurement system and detecting changes in the band shift.

On the other hand, it is also possible to screen for a substance that promotes the process of converting PI into lyso-PI with the use of the above system. Such compound is thought to promote extracellular release of GPI-anchored proteins. Thus, it is considered that such compound can be used for production of useful substances. Production of useful substances is described in detail below.

Another system for screening for a useful substance of the present invention is described below.

Specifically, it has been revealed that a GPI-anchored protein exists on a sphingolipid- or sterol-rich membrane portion of the cell membrane, which is generally referred to as a microdomain or lipid raft. A fraction corresponding to such microdomain can be biochemically isolated as a detergent-resistant membrane (DRM) fraction which is not solubilized by a detergent Triton X-100 (1%). Bagnat et al. revealed that yeasts also have microdomains on which GPI-anchored proteins exist (Bagnat et al., 2000, Proc. Natl. Acad. Sci. USA 97, 3254-3259).

Meanwhile, it has been known that Gas1p, a GPI protein, cannot enter the DRM fraction in a case where an abnormality is present in a GUP1 gene product which converts lyso-PI into a pG1-form lipid during GPI lipid remodeling (Bosson, R., Jaquenoud, M., and Conzelmann, A. Mol. Biol. Cell 17: 2636-2645 (2006)). In addition, the present inventors discovered that an abnormality in a PER1 gene product prevents Gas1p from entering the DRM fraction. Thus, in general, when an abnormality occurs in GPI lipid remodeling, GPI-anchored proteins cannot enter a microdomain. Therefore, detection of the presence or absence of GPI-anchored proteins in the DRM fraction is indicative of the occurrence or nonoccurrence of an abnormality in lipid remodeling.

The above findings were confirmed by the following experiments.

[Experiment 1]

Isolating the DRM fraction was carried out according to Bagnat et al., 2000, Proc. Natl. Acad. Sci. USA 97, 3254-3259. A wild-type strain and a per1 disruptant corresponding to amounts with optical density of 30 at a wavelength of 600 nm (30 $OD_{600}$) were disrupted using glass beads. After the addition of Triton X-100 at a final concentration of 1% to the disrupted solution, density gradient centrifugation was carried out by using Optiprep®. Then, the resulting fractions were subjected to SDS-PAGE, followed by Western blotting. Detection of each fraction was performed using antibodies against Gas1p. As a result, in the case of the wild-type strain, Gas1p was found to most abundantly exist in the DRM fraction (fraction 2). However, in the case of the per1 disruptant, Gas1p was found to exist in soluble fractions (fractions 4-6) but substantially not in the DRM fraction.

These results indicate that, in the per1 disruptant, an abnormality occurs in localization of a GPI-anchored protein into a microdomain.

Considering these results and the fact that the PERLD1 gene expression level is increased in cancer cells, if a substance that can increase amounts of GPI-anchored proteins in the DRM fraction is obtained, such substance can be a potent candidate for an anticancer agent. Such substance can be discovered by culturing a per1 disruptant, a per1 disruptant with the overexpressed PER1 gene, a per1 disruptant with the overexpressed PERLD1 gene, or a wild-type strain in a medium into which a candidate compound of an anticancer agent or the like has been added.

Meanwhile, the present inventors have found that a GPI-anchored protein (Gas1p) is released into a medium in the per1 disruptant or the strain with the overexpressed PER1.

Such finding was obtained as a result of the following experiments.

[Experiment 2]

A wild-type strain, a per1 disruptant, a per1 disruptant with the overexpressed PER1 gene, and a per1 disruptant with the overexpressed PERLD1 gene were separately cultured overnight in a selective medium. Trichloroacetic acid (TCA) was added at a final concentration of 10% to each medium corresponding to an amount of cells of 10 $OD_{600}$. Then, proteins were precipitated by centrifugation. The precipitate was dissolved in PBS. SDS sample buffer was added thereto for SDS treatment. Thus, SDS-PAGE samples were obtained and Gas1p was detected by Western blotting. In the case of the wild-type strain, Gas1p was not substantially detected in the medium. However, in the cases of the per1 disruptant and the strain with the overexpressed PER1, Gas1p was detected in the medium, indicating the release of Gas1p into the medium.

Consequently, it is indicated that GPI-anchored proteins cannot stay in the vicinity of the cell surface either in a case where the lipid remodeling process is inhibited or promoted. Thus, a candidate compound of an anticancer agent or the like may be added into the medium upon culturing the per1 disruptant, the per1 disruptant with the overexpressed PER1 gene, the per1 disruptant with the overexpressed PERLD1 gene, or the wild-type strain, and the amounts of GPI-anchored proteins released into a medium may be measured. In particular, if a compound is found to decrease the amount of GPI-anchored proteins in the medium when the candidate compound for an anticancer agent is added to the medium upon culturing the per1 disruptant, the strain with the overexpressed PER1 gene, or the strain with the overexpressed PERLD1 gene, such compound may be a potent candidate for an anticancer agent.

As is apparent from the above descriptions, the per1 disruptant, the per1 disruptant with the overexpressed PER1 gene, the per1 disruptant with the overexpressed PERLD1 gene, and the wild-type strain of budding yeast may be test materials which may be used for effective screening for a substance that inhibits or promotes the GPI lipid remodeling process.

Meanwhile, as described above, extracellular release of GPI-anchored proteins indicates an abnormality in GPI lipid remodeling. Thus, an abnormality in the intracellular lipid remodeling process can be detected by measuring the amounts of GPI-anchored proteins released into the extracellular medium.

For instance, when the amounts of GPI-anchored proteins in blood increase, an abnormality in the lipid remodeling process in the cells of the subject's body is indicated. In addition, considering that the PERLD1 gene expression level is increased in cancer cells as described above, detection of such increase can also be used for early diagnostics or determination of the stage of the disease. In such case, examples of human GPI-anchored proteins to be detected include CEA (carcinoembryonic antigen) and alkaline phosphatase.

Further, examples of means of detecting GPI-anchored proteins include antibodies against such proteins and toxins that bind to GPI such as alpha-toxin, aerolysin, and Cry11Aa.

The method of the present invention is useful for production of GPI-anchored proteins or substances derived therefrom. When culturing cells with abnormalities in the GPI lipid remodeling process, such as the per1 disruptant, the per1 disruptant with the overexpressed PER1 gene, and the per1 disruptant with the overexpressed PERLD1 gene of budding yeast, it is possible to recover large amounts of GPI-anchored proteins more efficiently than when culturing the wild-type strain. When chemically or enzymatically treating sugar chains that have been added to a GPI-anchored protein, it is possible to recover sugar chains of mannan. It has been reported that mannan has many functions such as the interferon-inducing activity (Acta Virology, 1970, 14: 1-7), the macrophage-migration-inhibiting activity (Jpn. J. Microbiol., 1975, 19: 355-362), enhancing TNFα production (Microbiol. Immunol., 2002, 46: 503-512), and the like. In addition, the following functions have been reported in patent publications: antitumor activity of linear mannan (JP Patent Publication (Kokai) No. 54-97692 A (1979)) and antitumor activity of phosphorated mannan against ascitic tumor (JP Patent Publication (Kokai) No. 58-121216 A (1983)). Considering these reports, it is expected that mannan can be used for foods or pharmaceuticals as an agent with a variety of functions.

As described in Example 8 below, as a result of analysis of a functional domain of Per1 protein, histidines at positions 177 and 326 were found to be essential for the function of this domain. In addition, since PERLD1 is a functional homolog of PER1, the function of the Per1 or PERLD1 protein can be effectively inhibited by creating a peptide antibody against the segment around these positions in the Per1 or PERLD1 protein.

Such antibody is expected to be capable of inhibiting a cancer which is induced due to the increase in PERLD1 expression level.

Specifically, an antigenic peptide of the segment around the position 177 or 326 in a Per1 protein is created and rabbits are immunized with such peptide such that antibodies produced in blood are obtained by blood collection. Then, the collected antibodies may be purified. In addition, monoclonal antibodies may be obtained by a conventional hybridoma method.

EXAMPLES

The present invention is hereafter described in greater detail with reference to the following examples, although the technical scope of the present invention is not limited thereto.

Example 1

Preparation of the PER1 Gene, the PERLD1 Gene, the Per1 Protein, and the PERLD1 Protein The PER1 gene was obtained by PCR using budding yeast (*Saccharomyces cerevisiae*) genomic DNA as a template. Primers used for the PCR were as follows. PER1F: 5'-AAAAactagtTGGAACATTGCACAAAGG-3' (SEQ ID NO: 5) PER1R-NheI: 5'-AAAAaagcttTTAgctagcGTA-CAATTGTCTATTACCCCAA-3' (SEQ ID NO: 6)

DNA fragments obtained by amplification were cleaved using restriction enzymes SpeI and HindIII. The resulting fragments were inserted into a budding yeast single copy vector pRS316 (Sikorski and Hieter, 1989, Genetics 122, 19-27) and nucleotide sequencing was conducted. The nucleotide sequence of the open reading frame region is represented by SEQ ID NO: 1. The terminator of GPI7 was inserted into the plasmid. The resulting plasmid was introduced into yeast cells such that the PER1 gene was expressed therein. Thus, a protein having the amino acid sequence represented by SEQ ID NO: 2 was obtained.

The PERLD1 gene was obtained by PCR using a plasmid DNA of NIH mammalian gene collection clone No. 3855206 as a template. Primers used for the PCR are as follows.

PERLD1-F: 5'-AAAAGAATTCatggccggcctggcggcg-3' (SEQ ID NO: 7)

PERLD1-R: 5'-AAAAGTCGACtcagtccagcttgaacttgtcc-3' (SEQ ID NO: 8)

DNA fragments obtained by amplification were cleaved using restriction enzymes EcoRI and SalI. The resulting fragments were inserted into a budding yeast multi copy vector YEp352GAP II (Abe et al., 2003, Glycobiology 13, 87-95) and nucleotide sequencing was conducted. The nucleotide sequence of the open reading frame region is represented by SEQ ID NO: 3. The plasmid was introduced into yeast cells such that the PERLD1 gene was expressed therein. Thus, a protein having the amino acid sequence represented by SEQ ID NO: 4 was obtained.

It was confirmed that Calcofluor White (CFW) sensitivity and high temperature sensitivity of the per1 disruptant were restored by the Per1 and PERLD1 proteins and, thus, the proteins were functional.

Example 2 per1 Disruptant Phenotype Analysis

Figure 3A:
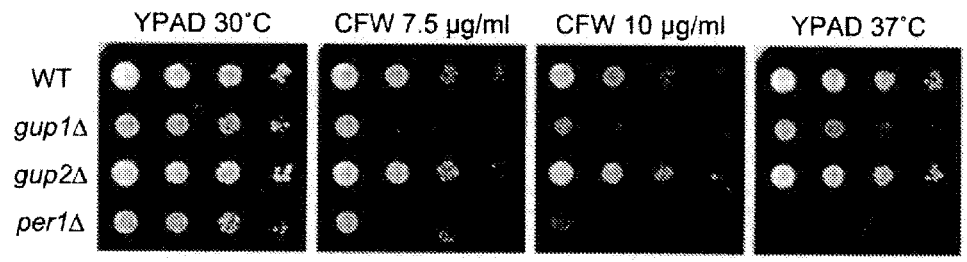
FIG. 3A shows the plates and FIGS. 3B and 3C show the results of Western blotting, both indicating properties of a per1 disruptant.

With the use of a disruptant of the PER1 gene (per1Δ) of budding yeast (*Saccharomyces cerevisiae*) obtained from EUROSCARF, temperature sensitivity and sensitivity of an agent (CFW) that detect defects in the cell wall were confirmed by a SPOT test. For comparison, a wild-type strain and a disruptant of the gene GUP1, a gene involved in the remodeling of the GPI-anchored protein, (gup1Δ) were used. In the case of the wild-type strain, cell growth was observed under any of the conditions. In the case of the gup1Δ strain, CFW sensitivity was observed as reported (FIG. 3A). On the contrary, in the case of the per1Δ strain, sensitivity was observed with the use of 7.5 μg/mL or more of CFW. Further, temperature sensitivity was observed at 37° C. (FIG. 3A). Accordingly, it was suggested that per1Δ would exhibit an abnormality in cell wall synthesis.

Figure 3B:
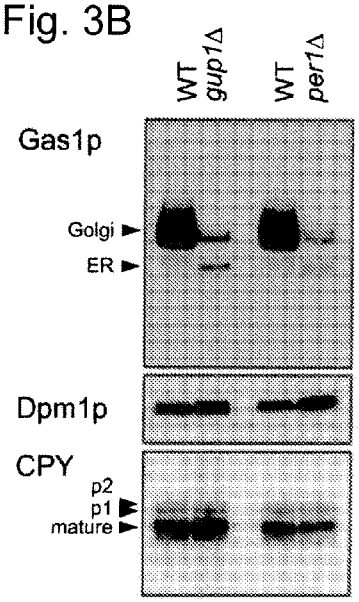

Subsequently, in order to examine involvement of this gene in GPI-anchored protein synthesis, the wild-type strain, the gup1Δ strain, and the per1Δ strain were examined by Western blotting for Gas1p, a representative yeast GPI-anchored protein. As a result, the Golgi-form Gas1p was found to significantly decrease in the cases of the gup1Δ and the per1Δ strains compared to the wild-type (FIG. 3B). Meanwhile, the endoplasmic rediculum (ER)-form Gas1p was detected in the cases of these deficient strains (FIG. 3B).

Figure 3C:
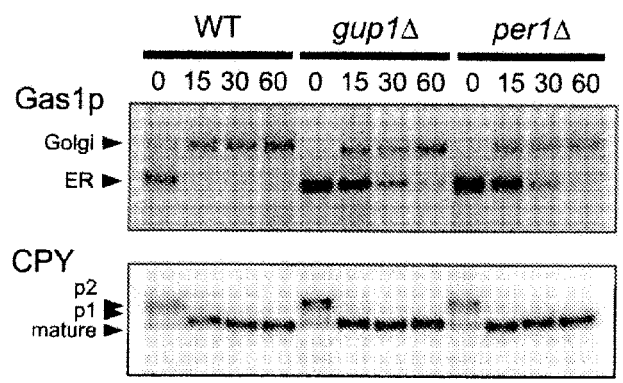

Further, a newly-synthesized protein was labeled with $^{35}S$ (EXPRE$^{35}S^{35}S$ Protein Labeling; Perkin Elmer) and ER-to-Golgi transport of Gas1p was examined by pulse-chase analysis. The analysis was carried out according to Sutterlin et al., 1997, J. Cell Sci. 110, 2703-2714. In the case of the gup1Δ strain, it has been revealed that ER-to-Golgi transport of Gas1p is delayed. In the case of the wild-type strain, almost 100% of Gas1p was transported to the cell membrane through the Golgi 15 minutes after pulse chasing. However, it was revealed that ER-to-Golgi transport is delayed in the case of the per1Δ strain, as with the case of the gup1Δ strain (FIG. 3C). On the other hand, ER-Golgi transport of a non-GPI anchor type protein carboxyl peptidase Y (CPY) was observed to the same extent as in the case of the wild-type strain (FIG. 3C).

Accordingly, it was revealed that PER1 is a gene involved in modification or transport of GPI-anchored proteins.

Example 3

Functions of the PERLD1 Gene in Yeast

Next, proteins homologous to the Per1 protein were searched on BLAST. *Candida albicans* XP_720676, *Drosophila melanogaster* AAM70807, rice AAT07554, *Arabidopsis thaliana* AAG10825, mice NP_001028709, human NP_219487 (PERLD1), and the like were listed. It has been revealed that the gene encoding human NP_219487 is located at a genome position 17q12 which is often amplified in gastric and breast cancer cells, and the expression of this gene actually increases in cell lines derived from patients with such cancer (Nezu et al., 2002, Jpn. J. Cancer Res. 93, 1183-1186).

Figure 4A:
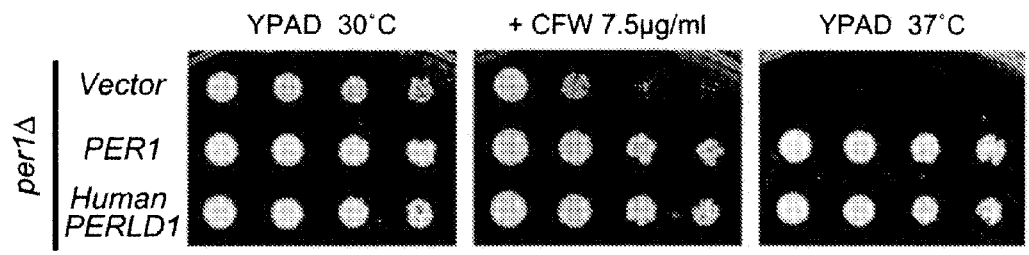
FIG. 4A shows the plates and FIG. 4B shows the results of Western blotting, both indicating that the function of the human PERLD1 gene is identical to that of the yeast PER1 gene.

The human PERLD1 gene was cloned by PCR and introduced into a yeast per1Δ strain. The phenotype of the per1Δ strain into which the gene had been introduced were confirmed by a SPOT test. As a result, CFW sensitivity and temperature sensitivity, the phenotypes of the per1Δ strain, were restored in the strain into which the gene had been introduced (FIG. 4A).

Figure 4B:
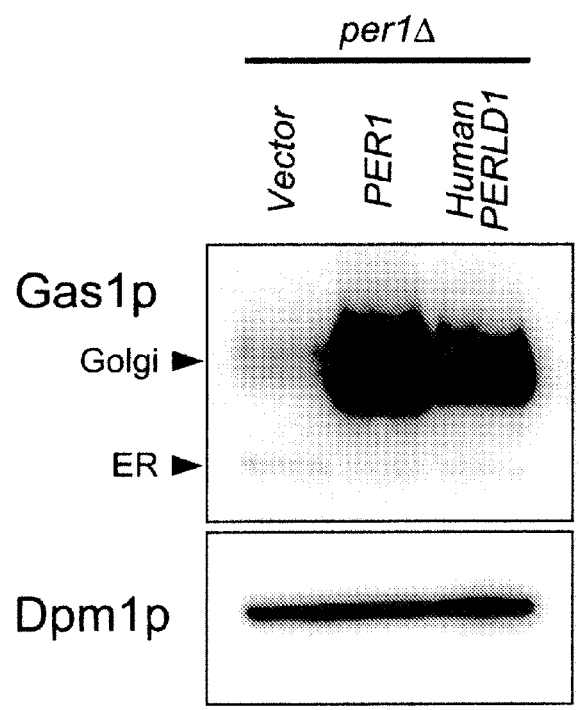

Further, when such strain was examined by Western blotting for Gas1p, the amount of Gas1p was found to be restored while decreases in the amount of Gas1p were observed in per1Δ (FIG. 4B).

Based on the above results, it was revealed that human PERLD1 is a functional homolog of yeast PER1.

Example 4

Analysis of Membrane Localization of a GPI-Anchored Protein Gas1

It has been revealed that a GPI-anchored protein exists on a sphingolipid- and sterol-rich membrane portion of the cell membrane, which is generally referred to as a microdomain or lipid raft. A fraction corresponding to such microdomain can be biochemically isolated as a detergent-resistant membrane (DRM) fraction which is not solubilized by a detergent Triton X-100 (1%). Bagnat et al. revealed that yeasts also have microdomains on which GPI-anchored proteins exist (Bagnat et al., 2000, Proc. Natl. Acad. Sci. USA 97, 3254-3259).

Figure 5:
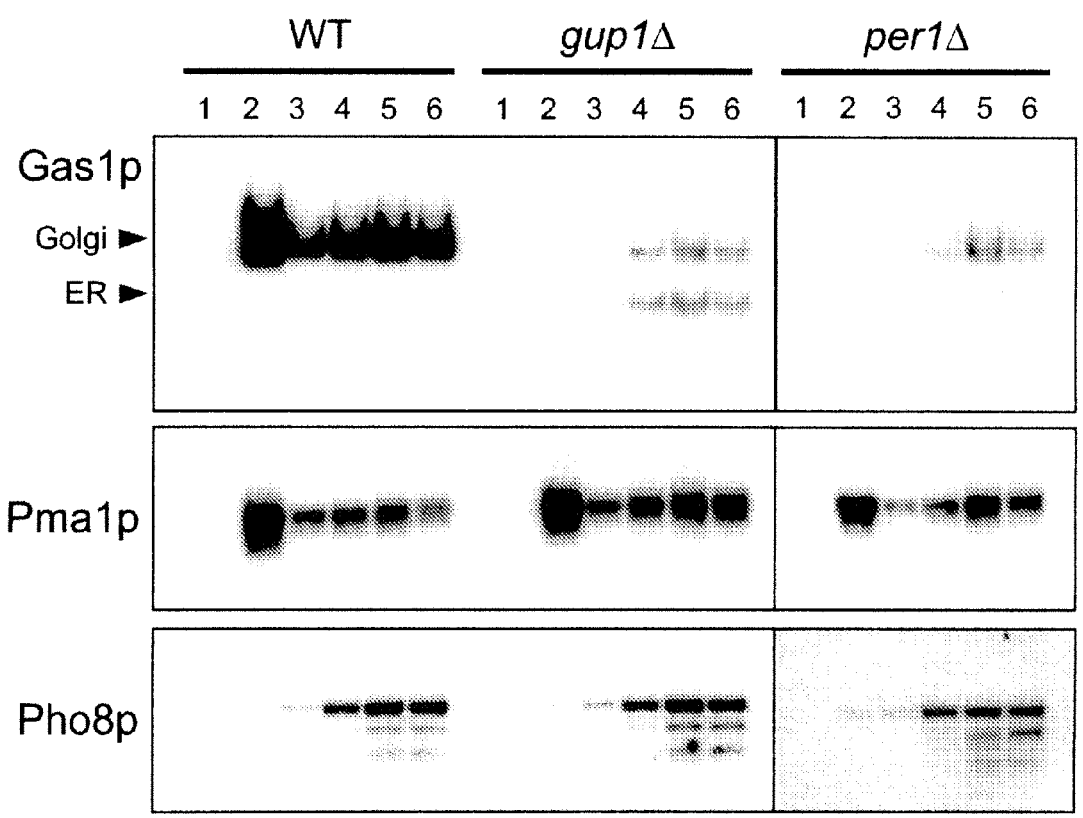
FIG. 5 shows the results of Western blotting indicating that Gas1p cannot exist in a detergent-resistant membrane (DRM) fraction in the case of a per1 disruptant.

Isolation of the DRM fraction was carried out according to Bagnat et al., 2000, Proc. Natl. Acad. Sci. USA 97, 3254-3259. A wild-type strain, a gup1Δ strain, and a per1Δ strain were cultured (until reaching 30 $OD_{600}$) and disrupted using glass beads. After the addition of Triton X-100 at a final concentration of 1% to the disrupted solution, density gradient centrifugation was carried out by using Optiprep®. Then, the resulting fractions were subjected to SDS-PAGE, followed by Western blotting. Detection of each fraction was carried out using antibodies against Gas1p, Pma1p, and Pho8p. As a result of detection of Gas1p, a GPI-anchored protein, in the case of the wild-type strain, Gas1p was found to most abundantly exist in the DRM fraction (fraction 2). In the cases of the gup1Δ and the per1Δ strains, Gas1p was found to exist in soluble fractions (fractions 4-6) but substantially not in the DRM fraction (FIG. 5: the upper column). Detection was carried out using an antibody against Pma1p, a protein existing in the DRM fraction, or an antibody against Pho8p, a protein not existing in DRM, and there were no differences among the wild-type strain, gup1Δ, and per1Δ (FIG. 5: the middle and the bottom columns).

The above results suggest that the per1Δ strain has an abnormality in localization of a GPI-anchored protein into a microdomain.

Example 5

Lipid Analysis of GPI-Anchored Protein Gas1

In the case of the per1Δ strain, a GPI-anchored protein was unable to exist in a microdomain and, thus, it was suspected that there would be a deficiency in the lipid on the GPI anchor of the proteins. Therefore, it was attempted to detect the deficiency in lipid of a GPI-anchored protein with the use of Octyl-FF (GE Healthcare). The method according to Tashima et al., 2006, Mol. Biol. Cell 17, 1410-1420 was used. A plasmid expressing Flag-tagged Gas1p (Flag-Gas1p) was introduced into a wild-type strain, a gup1Δ strain, a per1Δ strain, and a gup1Δ per1Δ double disruptant. Flag-Gas1p was purified from the resulting strains with the use of anti-FLAG beads (Sigma). Flag-Gas1p was eluted twice with 100 μL of a solution containing 3× FLAG peptide (Sigma). Flag-Gas1p purified from each strain (10 μL) was dissolved in C buffer (0.1 M ammonium acetate, 5% 1-propanol, 0.03% NP-40) and then applied to an Octyl-FF column. A buffer (0.1 M ammonium acetate, 5% 1-propanol) and B buffer (100% 1-propanol) were used to increase 1-propanol concentration gradually and the fractions (1 mL each) were obtained. The obtained fractions were dried using a centrifugal vacuum dryer and was subjected to SDS-PAGE, followed by Western blotting using FLAG antibodies (Sigma) to detect Flag-Gas1p.

Figure 6:
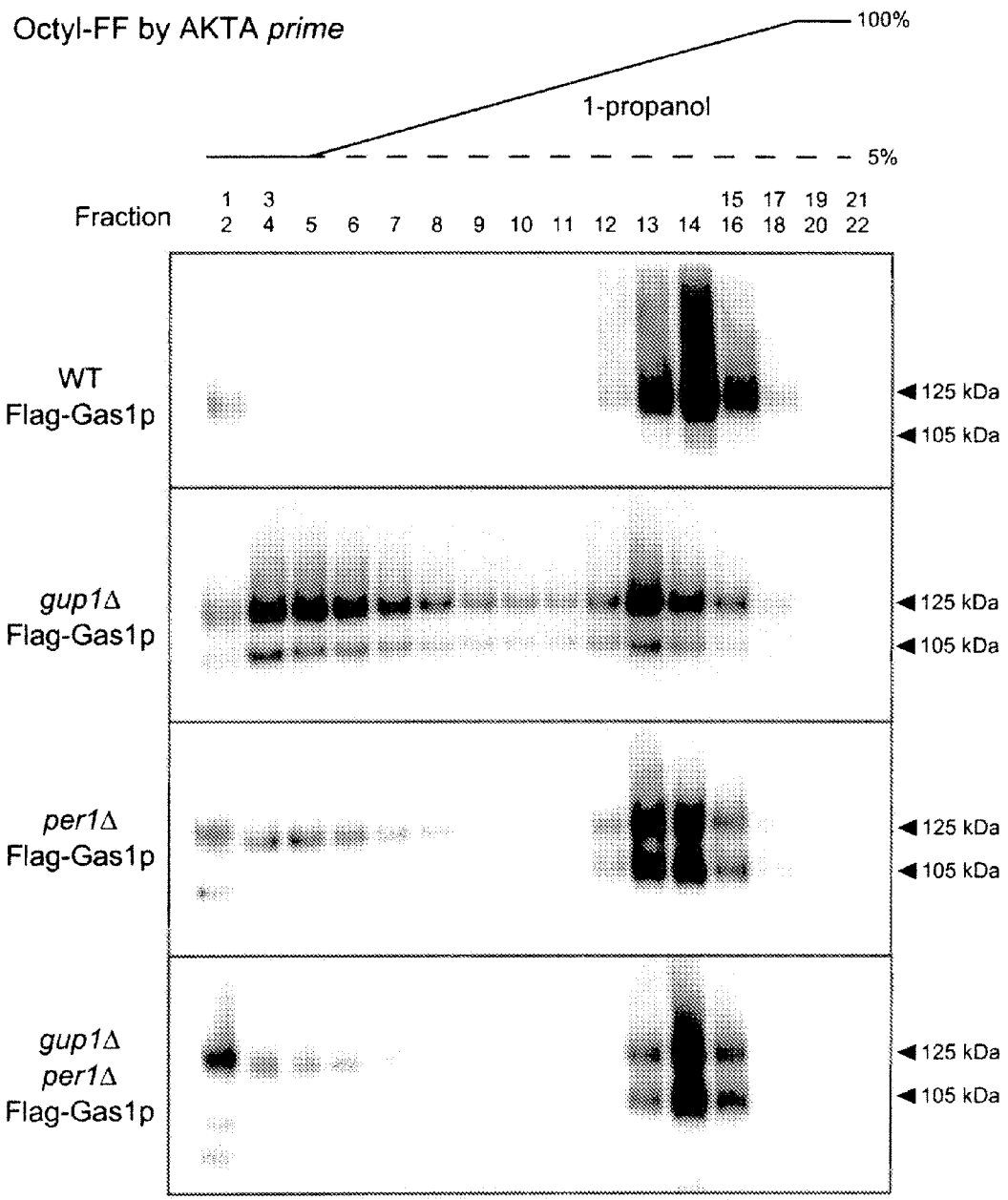
FIG. 6 shows the results of Western blotting for analysis of a lipid moiety of Gas1p.

Gas1p purified from WT (wild-type strain) was eluted in fractions 13-16 while Gas1p purified from the gup1Δ strain was eluted in the earlier fractions 3-8 (FIG. 6: the $1^{st}$ and $2^{nd}$ columns). Accumulation of lyso-form GPI was observed in the case of the gup1Δ strain. Thus, Gas1p purified from the gup1Δ strain is considered to be Gas1p containing a lyso-form lipid. Gas1p purified from the per1Δ strain behaved differently from Gas1p purified from WT and from gup1Δ (FIG. 6: the $3^{rd}$ column). The elution pattern of Gas1p purified from the gup1Δ per1Δ double disruptant was similar to that from per1Δ (FIG. 6: the $4^{th}$ column). Accordingly, it was suggested that PER1 would act prior to GUP1.

Example 6

Analysis of Lipid Moiety of GPI-Anchored Proteins

Because the above results suggested there was a deficiency in lipid on the GPI anchor of the protein, an analysis was conducted on the structure of phosphatidylinositol (PI) cleaved from the GPI-anchored protein. The analysis was carried out using the method according to Guillas et al., 2000, Methods Enzymol. 312, 506-515. A wild-type strain, a gup1Δ strain, a per1Δ strain, a gup1Δ per1Δ double disruptant, and a disruptant of the GPI7 gene (gpi7Δ), a gene involved in biosynthesis of GPI anchors, (20 $OD_{600}$ each) were allowed to incorporate [2-$^3$H] inositol (50 μCi) for 2 hours, followed by washing with chloroform/methanol to completely remove intracellular phospholipids. After solubilization of the proteins, glycoproteins were concentrated using 100 μL of ConA-sepharose (GE Healthcare). After washing, each resultant was allowed to react with pronase (Roche) at 37° C. for 16 hours, followed by boiling. After drying, the glycoproteins were treated with nitrous acid at 37° C. for 3 hours, subjected to a butanol extraction, and dried again. The thus extracted PI was resuspended in 15 μL of chloroform/methanol (1:1) and was applied to a silica 60 plate (Merck), followed by separation using a solvent system containing chloroform/methanol/0.25% KCl (55:45:10). Detection was carried out using Molecular Imager FX (Bio-Rad).

Figure 7:
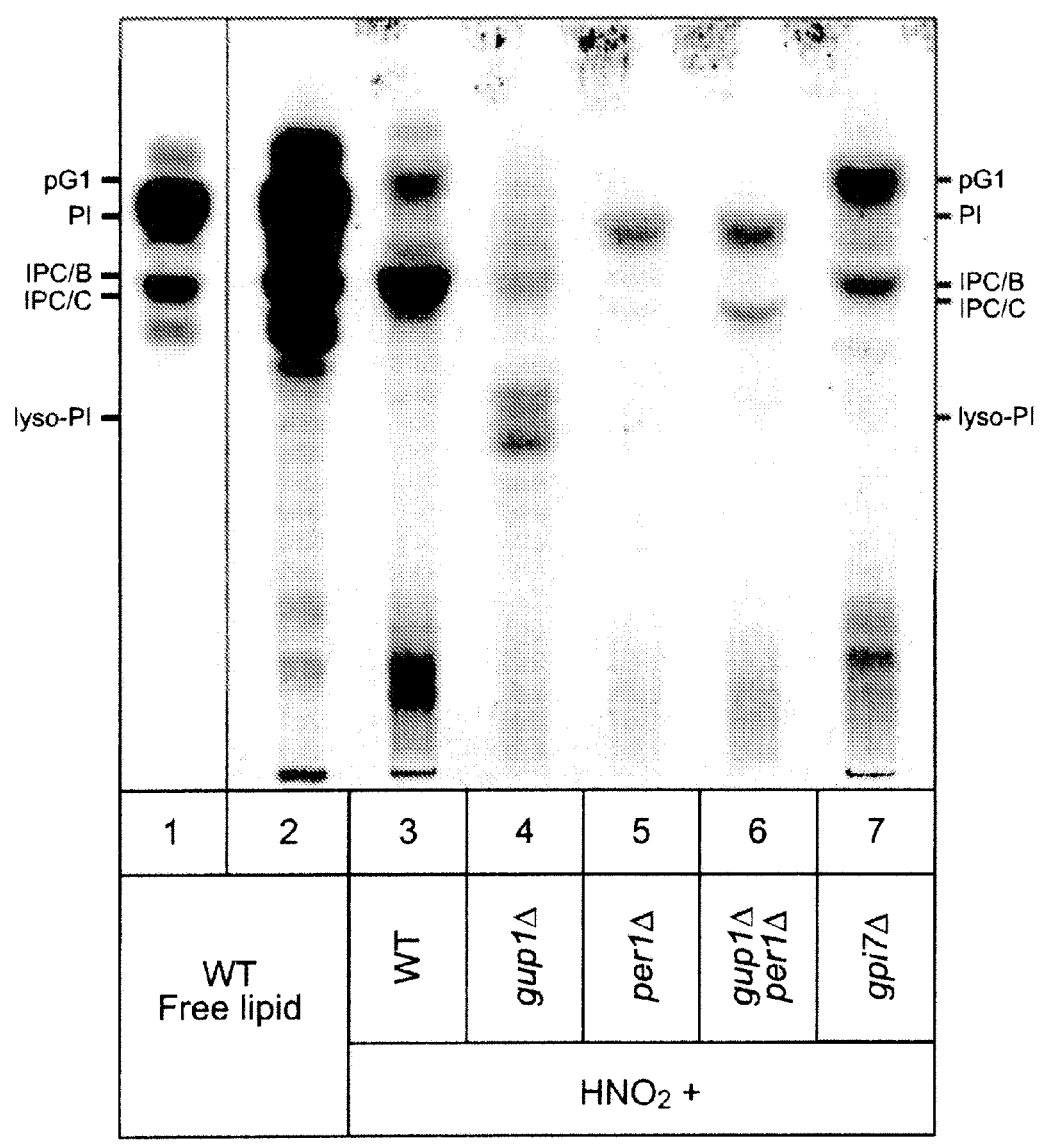
FIG. 7 shows the results of thin-layer chromatography for analysis of a lipid moiety of a GPI-anchored protein.

Consequently, in the case of the wild-type strain, diacylglycerol-type PI (pG1) comprising $C_{26}$ fatty acid, inositol-phosphoceramide/type B (IPC/B), and inositol-phosphoceramide/type C (IPC/C) were detected (FIG. 7: lane 3) as previously reported (Bosson et al. 2006, Mol. Biol. Cell 17, 2636-2645). In the case of the gup1Δ strain, a lyso form PI (lyso-PI) was detected (FIG. 7: lane 4) as previously reported (Bosson et al. 2006, Mol. Biol. Cell 17, 2636-2645). In addition, it has been reported that the gpi7Δ strain lacks IPC/C due to a deficiency in GPI remodeling in the Golgi (Benachour et al., 1999, J. Biol. Chem. 274, 15251-15261). The obtained results were the same as reported (FIG. 7: lane 7). On the other hand, in the case of the per1Δ strain, diacylglycerol-form PI comprising a short-chain fatty acid was exclusively detected (FIG. 7: lane 5). In the case of the gup1Δ per1Δ double disruptant, diacylglycerol-form PI comprising a short-chain fatty acid was detected as with the case of the per1Δ strain. In this case, IPC/C was additionally detected (FIG. 7: lane 6).

Based on the facts that the GPI lipid remained as PI in the case of the per1Δ strain and that the lipid remodeling pathway of GPI-anchored proteins is represented as "PI→lyso-PI→pG1→IPC," it was suggested that PER1 would be involved in a lyso-form formation reaction represented as "PI→lyso-PI."

Example 7

Analysis of in vitro Per1p Activity

In order to further confirm the above results, in vitro Per1p activity was determined. Flag-Gas1p (200 μL) that had been purified from the per1Δ strain in the manner described in Example 5 was concentrated by centrifugation (Apollo, 70 kDa, 7 mL), followed by washing 3 times with a TNP buffer (100 mM Tris-HCl (pH 7.5), 0.1% NP-40). The resultant was diluted with a TNP buffer to 200 μL and stored at −80° C. until use.

In addition, for preparing the membrane fraction, yeast cells (20 OD$_{600}$) were washed with TM buffer (100 mM Tris-HCl (pH 7.5), 10 mM MgCl$_2$) and resuspended in 200 μL of TM buffer, followed by disruption using glass beads. After cell walls were removed by centrifugation, the resultant was subjected to centrifugation at 13,000×g for 20 minutes. Then, the resulting pellet was resuspended in 100 μL of TM buffer and stored at −80° C. until use.

The reaction was carried out as follows.

| | Stock | |
| --- | --- | --- |
| Microsome in TM | 10 OD/50 μL | 50 μL |
| Flag-Gas1p in TNP | | 30 μL |
| ATP (5 mM) | 100 mM | 10 μL |
| DTT (1 mM) | 500 mM | 0.4 μL |
| CaCl$_2$ (5 mM) | 100 mM | 10 μL |
| MgCl$_2$ (10 mM) | 1 M | 2 μL |
| Tris-HCl, pH 7.5 (100 mM) | 1 M | 20 μL |
| H$_2$O | | 77.6 μL |
| Total | | 200 μL |

The reaction solution was allowed to stand on ice for 10 minutes, followed by incubation at 37° C. for 30 minutes. The reaction was terminated by adding 2 μL of 1 M NaN$_3$/NaF solution. TNE buffer (700 μL: 50 mM Tris-HCl (pH 7.5), 150 mM NaCl, 5 mM EDTA) was added thereto and then 100 μL of 10% NP-40 solution was added thereto. The resultant was solubilized at 4° C. for 1 hour, followed by centrifugation at 13,000×g for 15 minutes to remove the insoluble components. Anti-FLAG beads (20 μL) were added thereto, followed by incubation at 4° C. for 3 hours. The beads were washed 4 times and Flag-Gas1p was eluted twice using 50 μL of 3× FLAG peptide. C buffer (500 μL) used in Example 5 was added to the total amount of the purified Flag-Gas1p. The resultant was applied to an octyl column as described in Example 5. Then, each fraction was dried and subjected to SDS-PAGE, followed by Western blotting to detect Flag-Gas1p.

On the other hand, Flag-Gas1p was prepared in the same manner for comparison. Then, Flag-Gas1p was allowed to react with phospholipase A$_2$ (PLA$_2$) and the buffer alone. D buffer (500 μL: 100 mM Tris-HCl (pH 7.5), 10 mM CaCl$_2$, 0.1% NP-40) was added to 30 μL of Flag-Gas1p solution and 180 units of PLA$_2$ (Sigma) were also added thereto. The resultant was reacted overnight at 37° C., followed by centrifugation at 13,000×g for 15 minutes to remove the insoluble components. Anti-FLAG beads (20 μL) were added thereto, followed by incubation at 4° C. for 3 hours. The beads were washed 4 times and Flag-Gas1p was eluted twice using 50 μL of 3× FLAG peptide. C buffer (500 μL) used in Example 5 was added to the total amount of the purified Flag-Gas1p. The resultant was applied to an octyl column as described in Example 5. Then, each fraction was dried and subjected to SDS-PAGE, followed by Western blotting to detect Flag-Gas1p.

Figure 8:
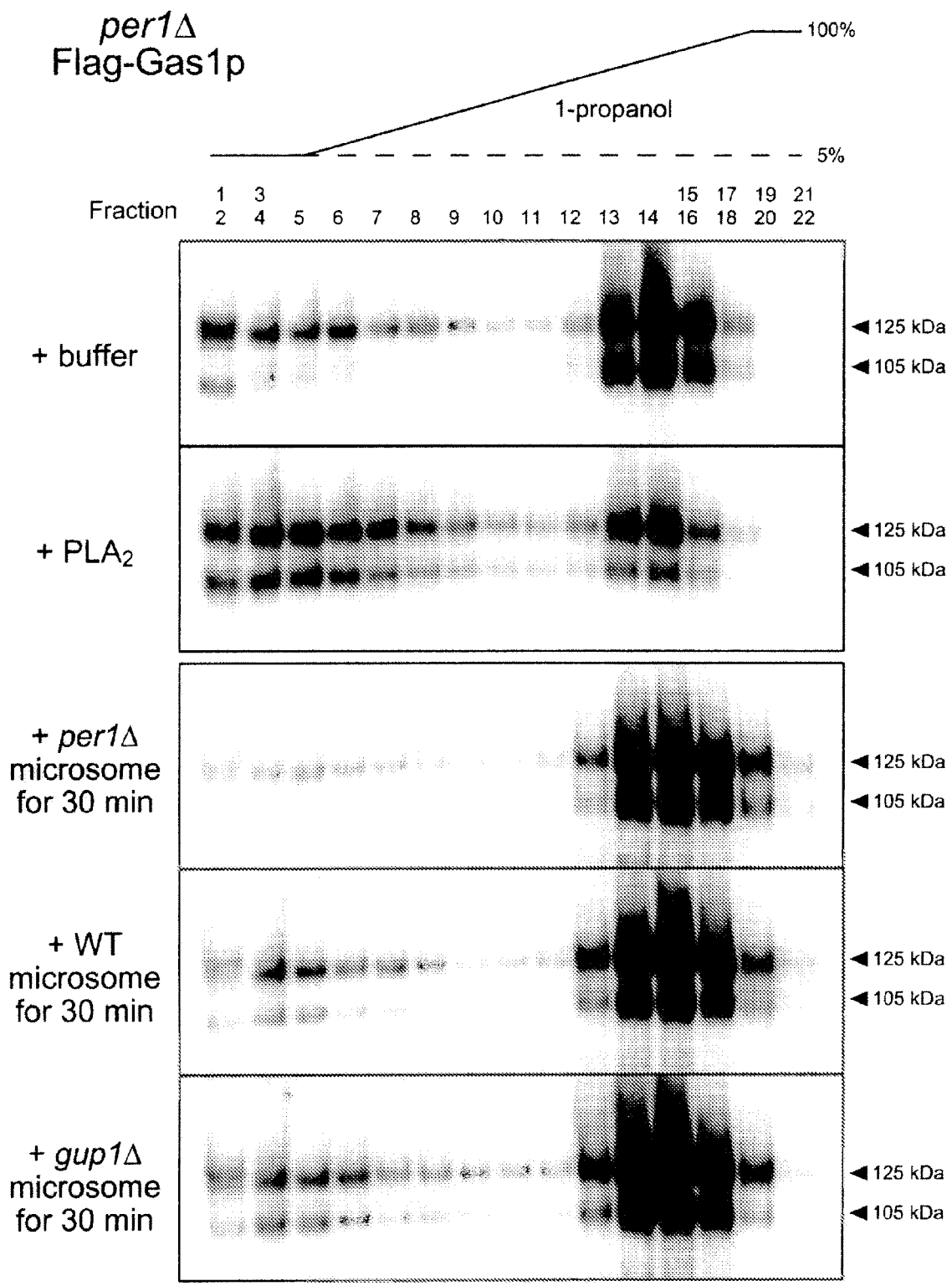
FIG. 8 shows the results of Western blotting indicating changes in a lipid moiety when Gas1p extracted from a per1 disruptant is reacted with membrane fractions derived from a variety of cells.

As a result, when reacted with the buffer alone, the elution pattern of Flag-Gas1p from the octyl column was identical to the pattern of that from the per1Δ strain (FIG. 8: the 1$^{st}$ column). On the contrary, when reacted with PLA$_2$, the band significantly shifted to the earlier fractions and, thus, a pattern similar to that purified from the gup1Δ strain was observed (FIG. 8: the 2$^{nd}$ column and FIG. 6: the 2$^{nd}$ column).

In addition, Flag-Gas1p purified from the per1Δ strain was allowed to react with a membrane fraction prepared from the wild-type strain, the gup1Δ strain, or the per1Δ strain. When reacted with a membrane fraction derived from the per1Δ strain, there was almost no change in the elution pattern. On the contrary, when reacted with a membrane fraction derived from the wild-type or the gup1Δ strain, the band shifted to the earlier fractions (FIG. 8: the 3$^{rd}$ to 5$^{th}$ columns). Accordingly, it has been revealed that PER1 is necessary for lyso-form formation in the remodeling of a GPI lipid moiety.

Example 8

Analysis of Functional Domains of Per1p

Figure 9A:
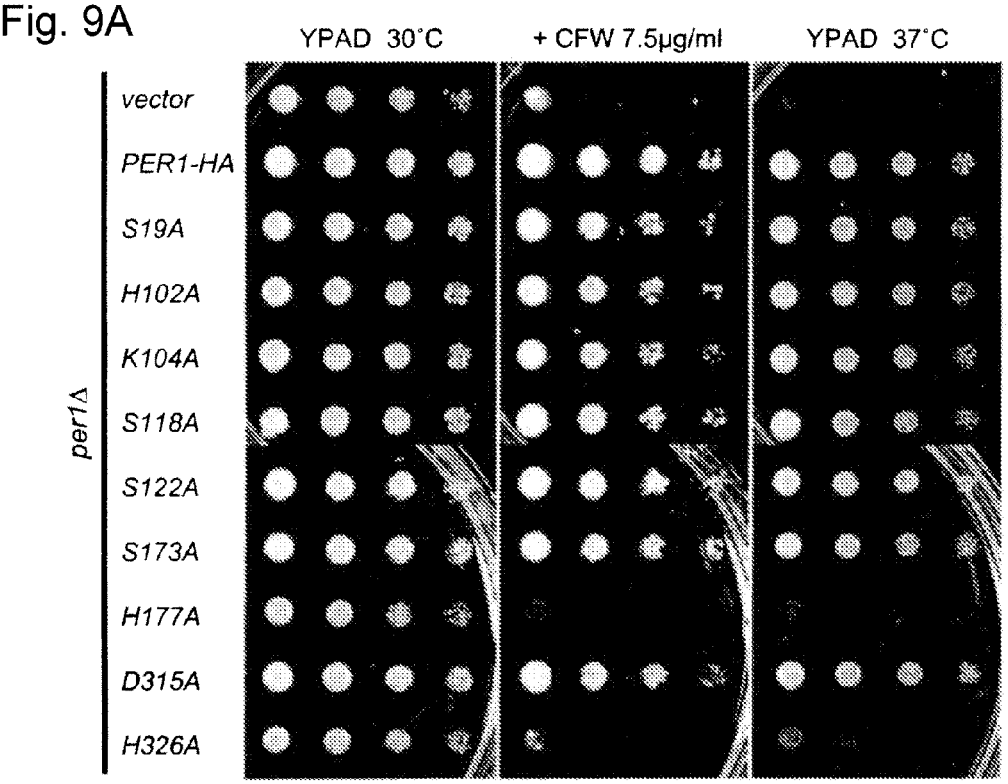
FIG. 9A shows the plates and FIG. 9B shows the results of Western blotting for analysis of characteristics of the Per1 protein upon mutagenesis.
Figure 9B:
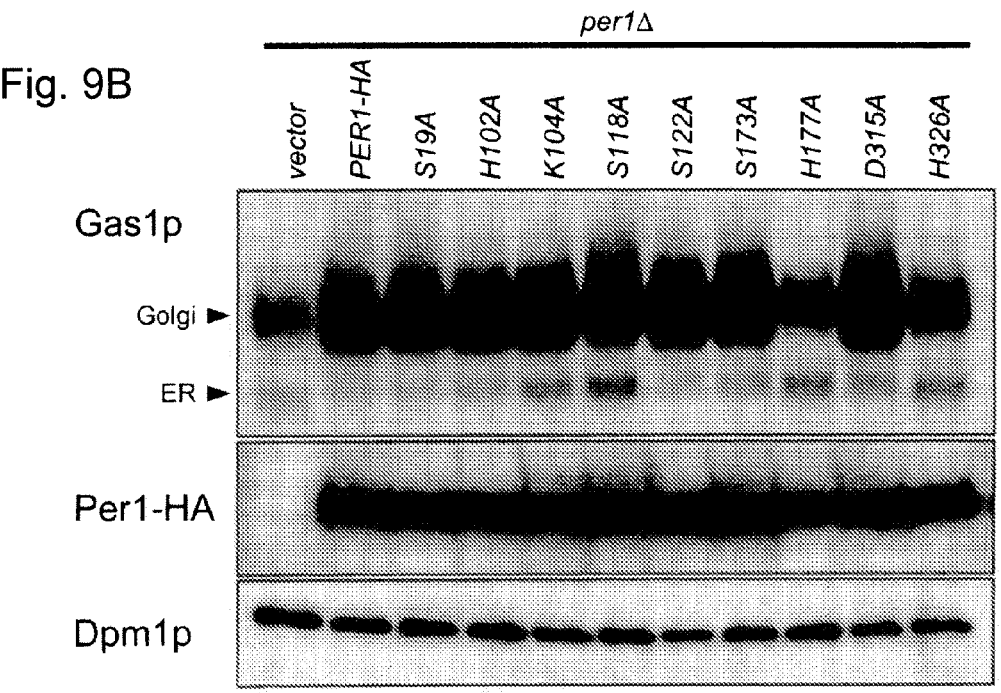

PER1 is involved in lyso-form formation in the lipid remodeling of a GPI-anchored protein. Thus, in order to elucidate the domains of Per1 protein involved in such function, amino acids conserved in PER1 homologues of from yeast to human were substituted with Alanine (A). A plasmid was constructed in a manner such that a fusion protein comprising a Per1 protein with 3× HA tag at its carboxy terminal was expressed using the promoter of PER1 itself. The strain obtained by introducing the plasmid (pRS316T-PER1HA), from which the above fusion protein is expressed, into the per1Δ strain restored all phenotypes exhibited by the per1Δ strain (CFW sensitivity, temperature sensitivity, and decreases in Gas1p). Thus, it was revealed that such fusion protein (Per1-HA) has a function identical to that of the Per1 protein. With the use of a pRS316T-PER1HA plasmid, the following nine positions were substituted with "A" by Site-directed mutagenesis (Stragagene): Serine (S) 19, Histidine (H) 102, Lysine (K) 104, S118, S122, S173, H177, Aspartic acid (D) 315, and H326. These mutant plasmids were separately introduced into the per1Δ strain. The per1Δ strains into which mutant plasmids had been introduced were evaluated by a SPOT test and Western blotting of Gas1p (FIG. 9).

As a result, the Per1 protein was found not to function in the strains in which Histidine at position 177 or 326 had been substituted with Alanine, while the strain contained the protein. Therefore, it has been revealed that regions in the vicinities of these amino acids play an important role in the function of Per1p.

Example 9

Release of a GPI-Anchored Protein Gas1 into the Medium Due to the Disruption or Overexpression of PER1

The results of the aforementioned experiments suggested that PER1 would be involved in the lipid remodeling of GPI-anchored proteins. Thus, influences of PER1 upon localization of a GPI-anchored protein Gas1p was examined. First, a strain with overexpressed PER1 was created. The yeast PER1 gene was cloned by PCR and inserted into an overexpression vector YEp352GAPII. The obtained plasmid (YEp352GAP-PER1), with which PER1 would be overexpressed, was introduced into a yeast wild-type strain. Phenotypes of the wild-type strain into which the gene had been introduced (PER1OP strain) were examined by a SPOT test. The PER1OP strain into which the gene had been introduced did not exhibit CFW sensitivity and temperature sensitivity, the phenotypes of per1Δ.

Subsequently, in order to examine influences of PER1 upon localization of a GPI-anchored protein Gas1p, Gas1p released into medium was detected. The PER1OP strain, a per1Δ strain, and controls (gup1Δ and wild-type strains) were separately cultured overnight in a selective medium. Trichloroacetic acid (TCA) was added to each strain (10 $OD_{600}$) to a final concentration of 10%. Then, proteins were precipitated by centrifugation. The precipitate was dissolved in PBS and SDS sample buffer was added thereto for SDS treatment to obtain SDS-PAGE samples. Gas1p was detected by Western blotting.

Figure 10:
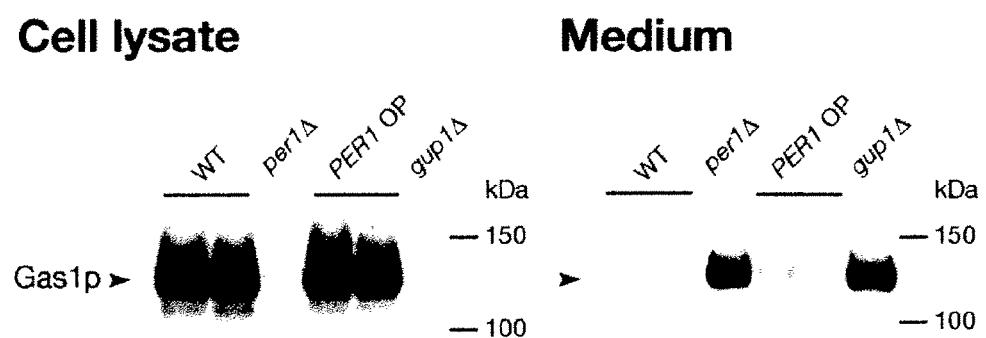
FIG. 10 shows the results of Western blotting indicating the relationship between the GPI lipid remodeling and GPI-anchored proteins released into the medium.

As a result, in the case of the wild-type strain, Gas1p was not detected in the medium, while Gas1p was detected in the medium in the cases of the gup1Δ and the per1Δ strains (FIG. 10). Further, in the case of the PER1OP strain, Gas1p was detected in the medium (FIG. 10). The results suggest that a GPI-anchored protein cannot stay on the cell surface and thus is extracellularly released when the process represented by "PI→lyso-PI" in lipid remodeling is inhibited or abnormally promoted.

What is claimed is:

1. A method for converting the phosphatidylinositol structure of a GPI-anchored protein to a lysophosphatidylinositol structure, comprising incubating said GPI-anchored protein in the phosphatidylinositol form in the presence of an enzyme, wherein:
   (i) said enzyme shares 92% or more homology with the amino acid sequence of SEQ ID NO: 2 or SEQ ID NO: 4; and
   (ii) said enzyme has the activity of converting the phosphatidylinositol form of a GPI-anchored protein to the lysophosphatidylinositol form.

2. A method for screening for a substance that promotes or inhibits the activity of an enzyme, comprising:
   (i) incubating a GPI-anchored protein in the phosphatidyliniositol form and said enzyme in the absence or presence of said substance; and
   (ii) detecting any change in the amount of the lysophosphatidylinositol form of said GPI-anchored protein,
wherein:
   (a) said enzyme shares 92% or more homology with the amino acid sequence of SEQ ID NO: 2 or SEQ ID NO: 4; and
   (b) said enzyme has the activity of converting the phosphatidylinositol form of a GPI-anchored protein to the lysophosphatidylinositol form.

3. The method according to claim 2, wherein the substance that inhibits the activity of the enzyme is a candidate substance for an anticancer agent.

* * * * *

SEQUENCE LISTING

<160> NUMBER OF SEQ ID NOS: 8

<210> SEQ ID NO 1
<211> LENGTH: 1074
<212> TYPE: DNA
<213> ORGANISM: Saccharomyces cerevisiae

<400> SEQUENCE: 1

```
atgaggttag ctgtggttgt gaccctactt gttcactgtt tcctagtgac atgctctcca      60
ggagataatt tagatgagtt tatagactgt acgtatgcgt gcgagtataa cagaagatgt     120
ccgaattccc aaataaacta cattgaccct gaaaccaaca tgtttcatga tattgagttt     180
ttcgataccc cgcctttgta ctctaagtta ttgttctggg attgtatctc agattgtgat     240
taccaatgtc agcacatcat tacgcgctgg agaattgacg aagaggaaga aatataccaa     300
ttccatggga aatggccatt tttgagagta ttggggactc aggaattctt ctcgacgata     360
ttcagtatag gtaactttat tccacattat aagggatttg taaagttttc tagaatcata     420
cgcgaagagg gagataggag gagaaaaaac agcagaagta tactgatttg gaactacctt     480
tacgttactg tggcggaat gttggcttgg acagcaagct cggtctttca ctgtcgtgat     540
ttgatcataa cggagaagct agattacttt ttcgcaggtt taactgtcct aacagggttt     600
catgcaatat ttgcaagaat gacttccatg ttcctgtacc ccaagatagc acaagcgttc     660
actgcgtcag ttgcggcaat ctttgccctg cacatcttga gactctatgt tgactggtcg     720
tacacataca acatgagatt caacattttt ttcggtgttt tacagtatat tttattgata     780
atgttatcat gccaaaacta ccatgctctg caaaagcaaa agctaatggg cgaattcaag     840
aaaaccgcgt actccagctt caagcggcaa atcttcaaac tgtgtgtcat tccaattctt     900
cttgtgattg taaccacaat ggccatgtca ttggaactgt ttgactttt tagttacgaa     960 tggcagattg atgcccatgc gctatggcat ctgtgcacaa tatggccctc gtgggtattg    1020
tacgactttt tcctcgagga ttatgcctat tggggtaata gacaattgta ctaa          1074
```

<210> SEQ ID NO 2
<211> LENGTH: 357
<212> TYPE: PRT
<213> ORGANISM: Saccharomyces cerevisiae

<400> SEQUENCE: 2

```
Met Arg Leu Ala Val Val Thr Leu Leu Val His Cys Phe Leu Val
1               5                   10                  15

Thr Cys Ser Pro Gly Asp Asn Leu Asp Glu Phe Ile Asp Cys Thr Tyr
            20                  25                  30

Ala Cys Glu Tyr Asn Arg Arg Cys Pro Asn Ser Gln Ile Asn Tyr Ile
        35                  40                  45

Asp Pro Glu Thr Asn Met Phe His Asp Ile Glu Phe Phe Asp Thr Pro
    50                  55                  60

Pro Leu Tyr Ser Lys Leu Leu Phe Trp Asp Cys Ile Ser Asp Cys Asp
65                  70                  75                  80

Tyr Gln Cys Gln His Ile Ile Thr Arg Trp Arg Ile Asp Glu Glu Glu
                85                  90                  95

Glu Ile Tyr Gln Phe His Gly Lys Trp Pro Phe Leu Arg Val Leu Gly
            100                 105                 110

Thr Gln Glu Phe Phe Ser Thr Ile Phe Ser Ile Gly Asn Phe Ile Pro
        115                 120                 125

His Tyr Lys Gly Phe Val Lys Phe Ser Arg Ile Ile Arg Glu Glu Gly
    130                 135                 140

Asp Arg Arg Arg Lys Asn Ser Arg Ser Ile Leu Ile Trp Asn Tyr Leu
145                 150                 155                 160

Tyr Val Thr Val Ala Gly Met Leu Ala Trp Thr Ala Ser Ser Val Phe
                165                 170                 175

His Cys Arg Asp Leu Ile Ile Thr Glu Lys Leu Asp Tyr Phe Phe Ala
            180                 185                 190

Gly Leu Thr Val Leu Thr Gly Phe His Ala Ile Phe Ala Arg Met Thr
        195                 200                 205

Ser Met Phe Leu Tyr Pro Lys Ile Ala Gln Ala Phe Thr Ala Ser Val
    210                 215                 220

Ala Ala Ile Phe Ala Leu His Ile Leu Arg Leu Tyr Val Asp Trp Ser
225                 230                 235                 240

Tyr Thr Tyr Asn Met Arg Phe Asn Ile Phe Phe Gly Val Leu Gln Tyr
                245                 250                 255

Ile Leu Leu Ile Met Leu Ser Cys Gln Asn Tyr His Ala Leu Gln Lys
            260                 265                 270

Gln Lys Leu Met Gly Glu Phe Lys Lys Thr Ala Tyr Ser Ser Phe Lys
        275                 280                 285

Arg Gln Ile Phe Lys Leu Cys Val Ile Pro Ile Leu Leu Val Ile Val
    290                 295                 300

Thr Thr Met Ala Met Ser Leu Glu Leu Phe Asp Phe Phe Ser Tyr Glu
305                 310                 315                 320

Trp Gln Ile Asp Ala His Ala Leu Trp His Leu Cys Thr Ile Trp Pro
                325                 330                 335

Ser Trp Val Leu Tyr Asp Phe Phe Leu Glu Asp Tyr Ala Tyr Trp Gly
            340                 345                 350

Asn Arg Gln Leu Tyr
        355
```

<210> SEQ ID NO 3
<211> LENGTH: 963
<212> TYPE: DNA
<213> ORGANISM: Homo sapiens

<400> SEQUENCE: 3

-continued

```
atggccggcc tggcggcgcg gttggtcctg ctagctgggg cagcggcgct ggcgagcggc    60
tcccagggcg accgtgagcc ggtgtaccgc gactgcgtac tgcagtgcga agagcagaac   120
tgctctgggg gcgctctgaa tcacttccgc tcccgccagc caatctacat gagtctagca   180
ggctggacct gtcgggacga ctgtaagtat gagtgtatgt gggtcaccgt gggctctac    240 ctccaggaag gtcacaaagt gcctcagttc atggcaagt ggcccttctc ccggttcctg    300
ttctttcaag agccggcatc ggccgtggcc tcgtttctca atggcctggc cagcctggtg   360
atgctctgcc gctaccgcac cttcgtgcca gcctcctccc ccatgtacca cctgtgtg     420 gccttcgcct gggtgtccct caatgcatgg ttctggtcca cagttttcca ccagggac     480 actgacctca cagagaaaat ggactacttc tgtgcctcca ctgtcatcct acactcaatc   540
tacctgtgct gcgtcaggac cgtggggctg cagcacccag ctgtggtcag tgccttccgg   600
gctctcctgc tgctcatgct gaccgtgcac gtctcctacc tgagcctcat ccgcttcgac   660
tatggctaca acctggtggc caacgtggct attggcctgg tcaacgtggt gtggtggctg   720
gcctggtgcc tgtggaacca gcggcggctg cctcacgtgc gcaagtgcgt ggtggtggtc   780 tgctgctgc aggggctgtc cctgctcgag ctgcttgact ccccaccgct cttctgggtc    840
ctggatgccc atgccatctg gcacatcagc accatccctg tccacgtcct cttttcagc    900 tttctggaag atgacagcct gtacctgctg aaggaatcag aggacaagtt caagctggac   960
tga                                                                 963
```

```
<210> SEQ ID NO 4
<211> LENGTH: 320
<212> TYPE: PRT
<213> ORGANISM: Homo sapiens

<400> SEQUENCE: 4
```

```
Met Ala Gly Leu Ala Ala Arg Leu Val Leu Leu Ala Gly Ala Ala Ala
1               5                   10                  15

Leu Ala Ser Gly Ser Gln Gly Asp Arg Glu Pro Val Tyr Arg Asp Cys
            20                  25                  30

Val Leu Gln Cys Glu Glu Gln Asn Cys Ser Gly Gly Ala Leu Asn His
        35                  40                  45

Phe Arg Ser Arg Gln Pro Ile Tyr Met Ser Leu Ala Gly Trp Thr Cys
    50                  55                  60

Arg Asp Asp Cys Lys Tyr Glu Cys Met Trp Val Thr Val Gly Leu Tyr
65                  70                  75                  80

Leu Gln Glu Gly His Lys Val Pro Gln Phe His Gly Lys Trp Pro Phe
                85                  90                  95

Ser Arg Phe Leu Phe Phe Gln Glu Pro Ala Ser Ala Val Ala Ser Phe
            100                 105                 110

Leu Asn Gly Leu Ala Ser Leu Val Met Leu Cys Arg Tyr Arg Thr Phe
        115                 120                 125

Val Pro Ala Ser Ser Pro Met Tyr His Thr Cys Val Ala Phe Ala Trp
    130                 135                 140

Val Ser Leu Asn Ala Trp Phe Trp Ser Thr Val Phe His Thr Arg Asp
145                 150                 155                 160

Thr Asp Leu Thr Glu Lys Met Asp Tyr Phe Cys Ala Ser Thr Val Ile
                165                 170                 175

Leu His Ser Ile Tyr Leu Cys Cys Val Arg Thr Val Gly Leu Gln His
            180                 185                 190
```

```
Pro Ala Val Val Ser Ala Phe Arg Ala Leu Leu Leu Met Leu Thr
    195                 200                 205

Val His Val Ser Tyr Leu Ser Leu Ile Arg Phe Asp Tyr Gly Tyr Asn
    210                 215                 220

Leu Val Ala Asn Val Ala Ile Gly Leu Val Asn Val Trp Trp Leu
225                 230                 235                 240

Ala Trp Cys Leu Trp Asn Gln Arg Arg Leu Pro His Val Arg Lys Cys
            245                 250                 255

Val Val Val Leu Leu Leu Gln Gly Leu Ser Leu Glu Leu
        260                 265                 270

Asp Phe Pro Pro Leu Phe Trp Val Leu Asp Ala His Ala Ile Trp His
    275                 280                 285

Ile Ser Thr Ile Pro Val His Val Leu Phe Phe Ser Phe Leu Glu Asp
    290                 295                 300

Asp Ser Leu Tyr Leu Leu Lys Glu Ser Glu Asp Lys Phe Lys Leu Asp
305                 310                 315                 320

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaaactagt tggaacattg cacaaagg                                          28

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaaaagctt ttagctagcg tacaattgtc tattacccca a                           41

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaagaattc atggccggcc tggcggcg                                          28

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaagtcgac tcagtccagc ttgaacttgt cc                                     32
```